United States Patent [19]

Vaillancourt

[11] Patent Number: 5,188,603
[45] Date of Patent: Feb. 23, 1993

[54] FLUID INFUSION DELIVERY SYSTEM

[76] Inventor: Vincent L. Vaillancourt, 14 Bunyan Dr., Livingston, N.J. 07039

[21] Appl. No.: 637,061

[22] Filed: Jan. 3, 1991

[51] Int. Cl.⁵ ............................................. A61M 37/00
[52] U.S. Cl. ..................................... 604/131; 604/151
[58] Field of Search .................... 604/82, 131, 121, 53, 604/65-67, 132, 133, 134, 135, 151, 152; 128/DIG. 12

[56] References Cited

U.S. PATENT DOCUMENTS

| | | | |
|---|---|---|---|
| 4,966,579 | 10/1990 | Palaschegg | 604/131 X |
| 5,059,174 | 10/1991 | Vaillancourt | 604/131 X |
| 5,069,668 | 12/1991 | Boydman | 604/131 X |

*Primary Examiner*—John D. Yasko
*Attorney, Agent, or Firm*—Francis C. Hand

[57] ABSTRACT

The infusion delivery system has a primary pump for delivering a medicament into an implanted catheter in a vein as well as a second pump for delivering saline solution into the catheter in order to keep the vein upon completion of the delivery of medicament of the vein. The secondary pump operates under a pressure less than that of the primary pump.

20 Claims, 3 Drawing Sheets

FLUID INFUSION DELIVERY SYSTEM

This invention relates to a fluid infusion delivery system. More particularly, this invention relates to a fluid delivery apparatus for infusing fluid into a vein.

As is known, various techniques have been used for infusing medication, drugs and the like into a patient from time to time, for example using a procedure often known as SASH. This procedure is used where a patient is provided with an indwelling catheter having an intermittent injection port or cap which permits a drug delivery device to be removed in order to permit the patient to be ambulatory. The SASH procedure consists generally of filling a needle syringe with saline solution and injecting the syringe through the cap in order to flush out any Heparin present in the indwelling catheter. In this respect, Heparin is usually present in order to prevent blood clotting in the catheter and injection port (cap). After the Heparin has been cleared, the desired drug is infused and thereafter, a second injection of saline solution is used to clear the line of all drugs. This, in turn, is followed by an infusion of Heparin in order to keep the line patent prior to reinjection of the drug.

In order to avoid the need for the SASH procedure, it has been known to provide an ambulatory disposable infusion delivery system as described in U.S. Pat. No. 4,867,743 and pending patent application Ser. No. 07/572,696, filed Aug. 23, 1990. As described, such systems employ, inter alia, a small infusion device to feed a small continuous flow of physiological saline solution into a catheter placed in a patient. As described, this continually infused solution prevents occluding of the catheter and, as no Heparin is required, an added drug may be injected into the indwelling catheter in the desired amount and at the desired time.

Other types of ambulatory disposable infusion delivery systems have also been known, such as described in U.S. Pat. No. 4,813,937 which employ a housing with a piston movable under the force of a stretched elastomeric member and a restrictor in a delivery line in order to deliver medication from the housing in a controlled amount. After delivery of the medication, the emptied housing is usually removed and disposed of while a fresh housing filled with medication, for example from two to sixty cubic centimeters, is put in place.

In cases where infusion pumps which are not ambulatory are used in combination with IV line sets or where an IV line set with a gravity feed is used of itself, it has been known to keep a line open (normally referred to as KVO-keep vein open) by infusing 15 to 25 milliliters per hour of fluid through the line into a patient. This quantity of fluid is used because, generally, the infusion pump is intermittent in operation thereby requiring a large quantity of fluid to overcome a period when the pump is shut down and blood is diffusing back up into the IV set. When a gravity set is used, it has been extremely difficult to maintain low volume drip rates without having periods of interruption when there is no flow. Hence, the KVO rate is approximately 20 to 25 milliliters per hour.

It has been found that for disposable ambulatory infusion pumps, particularly those using mechanical energy storage systems, there is an increasing incidence of clotted catheters and other access devices. This is due to the shut down of fluid flow once the infusion pump has discharged all of the storage capacity of fluid therefrom. There has been no provision for any excess capacity in order to provide for a KVO fluid flow rate. Generally, the quantity of medication to be infused is prescribed to be delivered over a given period of time. Hence, the quantity of medication controls the filling volume. When this volume is expended, fluid flow ceases and a potential clotting situation is then established. Should the pump be overfilled to give added time for the practitioner to discontinue medication and, concurrently, keep the access device from clotting, then the danger of overmedication becomes real and can cause equal or greater concerns than access device clotting.

It has been found in one study involving an AIDS patient that a pump operating in the normal mode at a rate of 60 milliliters per hour (that is, delivering approximately 1 milliliter per minute over approximately a 10 second period with a rest period of 50 seconds) that after approximately 6 hours, the AIDS virus was detected four feet up the IV Administration Set connected between the patient and the pump. This appeared to be due entirely to diffusion which more than compensated for the flow rate and washing effect when flow was in progress.

Accordingly, it is an object of the invention to maintain a positive pressure at all times at the opening of a catheter into a vein.

It is another object of the invention to prevent diffusion of blood from a vein into a catheter and infusion line of an ambulatory disposable infusion delivery system.

It is another object of the invention to provide for a KVO fluid flow rate into a vein access device using a non-medicament after infusion of a prescribed drug using a disposable ambulatory infusion pump.

Briefly, the invention provides a fluid infusion delivery system comprising an IV catheter for placement in a vein, a fluid line extending from the catheter for delivery of fluid thereto, a primary pump connected to the fluid line for delivering a predetermined dose of fluid (such as a medicament) to the line and a secondary pump connected to the fluid line for delivering a second fluid into the line under a continuous positive pressure to maintain the catheter patent in the absence of a delivery of fluid from the primary pump and sufficient to keep the vein open after delivery of a medicament dose.

The primary pump is particularly useful for delivering a medicament and is in the form of a disposable ambulatory infusion pump.

In one embodiment, the fluid infusion delivery system has a hub disposed between the two pumps and the infusion line to the catheter. In this embodiment, the hub has a first inlet in communication with the primary pump in order to receive fluid therefrom and a second inlet in communication with the secondary pump to receive fluid therefrom. In addition, the hub has an outlet in communication with the infusion line to deliver the respective fluid from the pumps. Further, a restrictor can be placed in the outlet of the hub for restricting the flow of fluid into the infusion line. Likewise, a filter may be placed between the restrictor and the hub inlets in order to filter the fluid delivered from the pumps.

In another embodiment, a restrictor and a filter may be placed in each inlet of the hub for restricting the flow of fluid therethrough while filtering the flow of fluid therein.

In still another embodiment, the hub may be in the form of a Y-site connector with the respective pumps connected to respective inlets of the connector.

In still another embodiment, the primary pump and secondary pump may be mounted within a common housing so as to provide a dual pump arrangement for fluid infusion. In this case, each pump may be of the spring and piston type or may be of bladder type or a combination thereof.

Where a disposable ambulatory infusion pump is used to deliver medication over a period of time, the secondary pump can be in the form of a storage container having a storage reservoir with an energy storage member in contact with the container. This secondary pump may be activated upon emptying of the medicament pump or alternatively begin dispensing fluid concurrent with the initial infusion of medicament. Where the connection of the secondary pump is made proximal (upstream) to a restrictor, the storage member which may be in the form of a spring, rubber or other mechanical energy means, generates a lower fluid pressure than the primary pump. As a consequence, fluid flow does not commence until the medicament-containing chamber of the primary pump has been emptied.

In accordance with the invention, micro-volumes of fluid are injected into the vein. As a result, the incidence of complications due to the injection of fluids not required by the body are substantially reduced. In this respect, it has been found that so long as there is a positive pressure (almost no matter what the pressure is) at the opening of the catheter into a vein, a number of advantages occur. These advantages include the absence of backflow, the absence of diffusion of blood back into the catheter and the maintenance of the catheter in a patent state.

The fluid delivery apparatus also eliminates the need for Heparin since there is no need for this drug in an intermittent injection therapy to keep the line patent.

Further, the apparatus permits a patient to be truly ambulatory after a medicament dose has been emptied from the primary pump and until the pump can be refilled or replaced. while his/her vein is kept open via the secondary pump. Also, the apparatus prevents the migration of unwanted organisms, such as viruses, from the body into the apparatus which is exterior to the body and which may potentially become a source for nosicomial infection.

These and other objects and advantages of the invention will become more apparent from the following detailed description taken in conjunction with the accompanying drawings wherein:

FIG. 1 schematically illustrates a fluid infusion delivery system in accordance with the invention;

Figure 6:
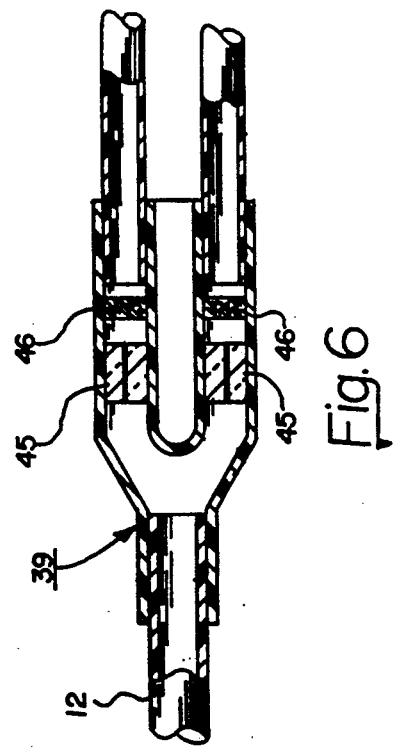
Figures 4, 5:
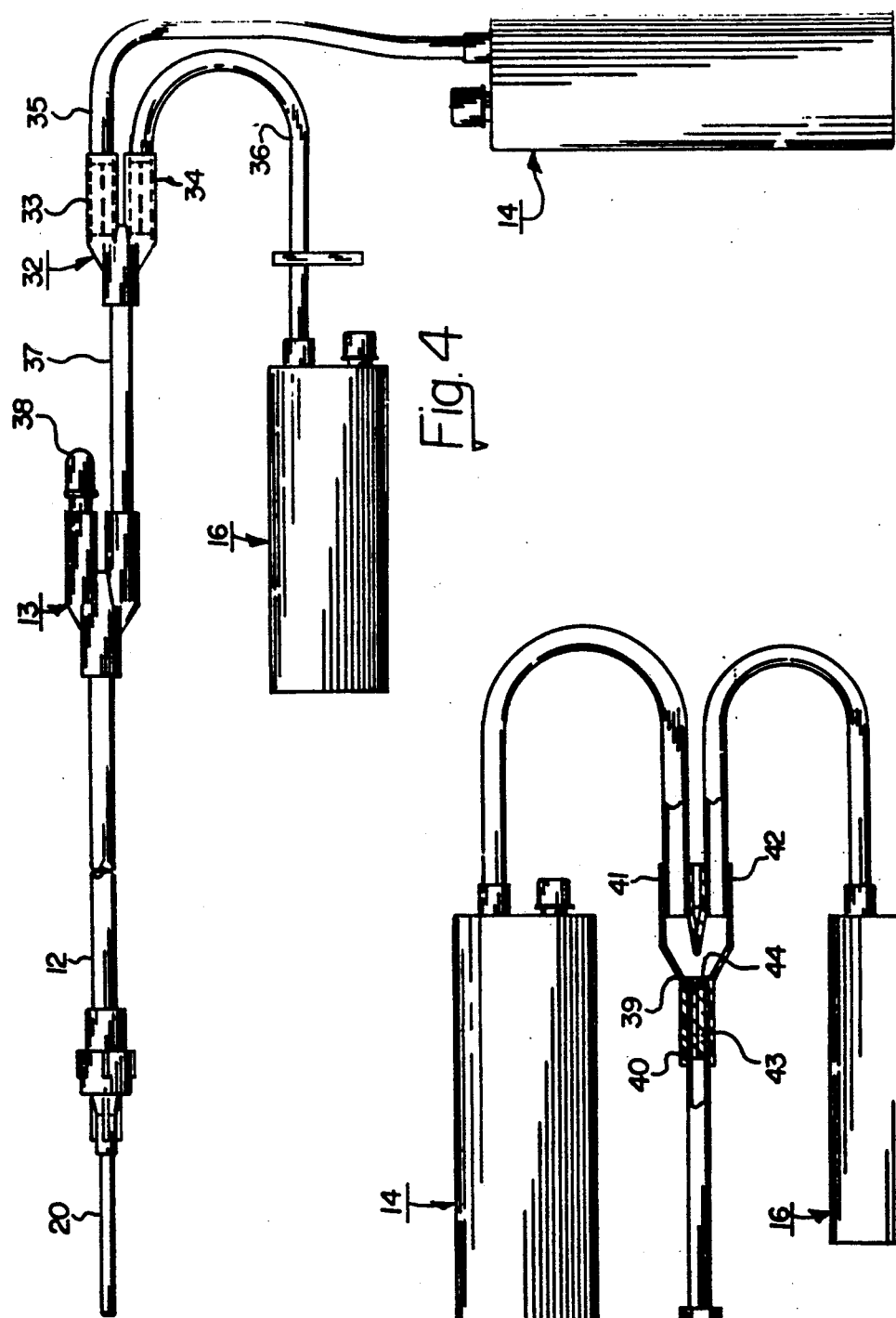
Figure 7:
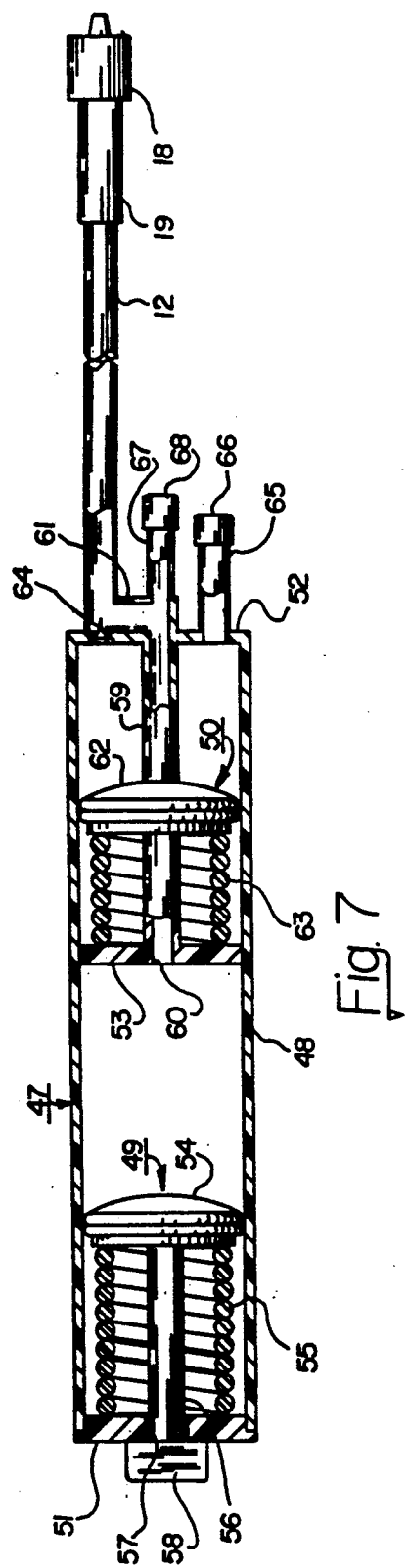
Figure 8:
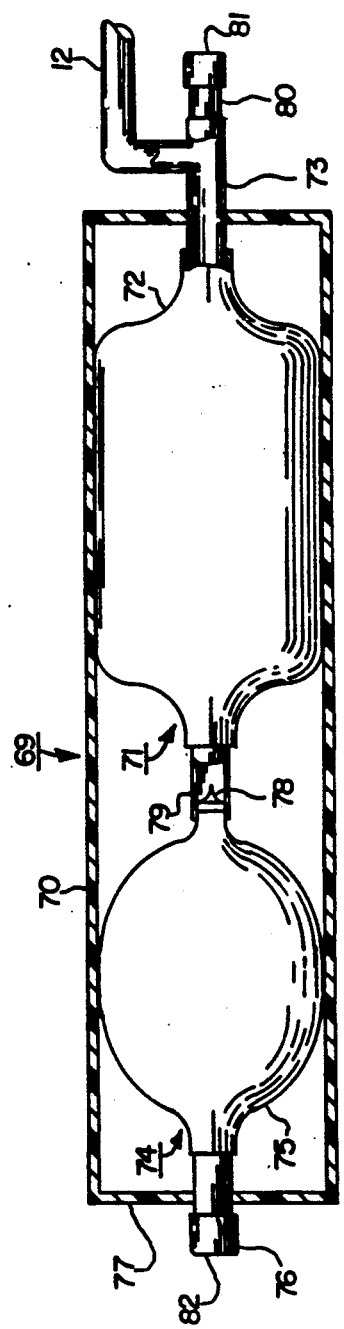

FIG. 4 schematically illustrates a modified fluid infusion delivery system in accordance with the invention;

FIG. 5 illustrates a further modified fluid infusion delivery system in accordance with the invention;

FIG. 6 illustrates a cross sectional view of a hub for connecting two pumps to an infusion line in accordance with the invention;

FIG. 7 illustrates a cross sectional view of a further modified embodiment of a dual pump constructed in accordance with the invention; and FIG. 8 illustrates a modified dual pump arrangement of bladder type in accordance with the invention.

Figure 1:
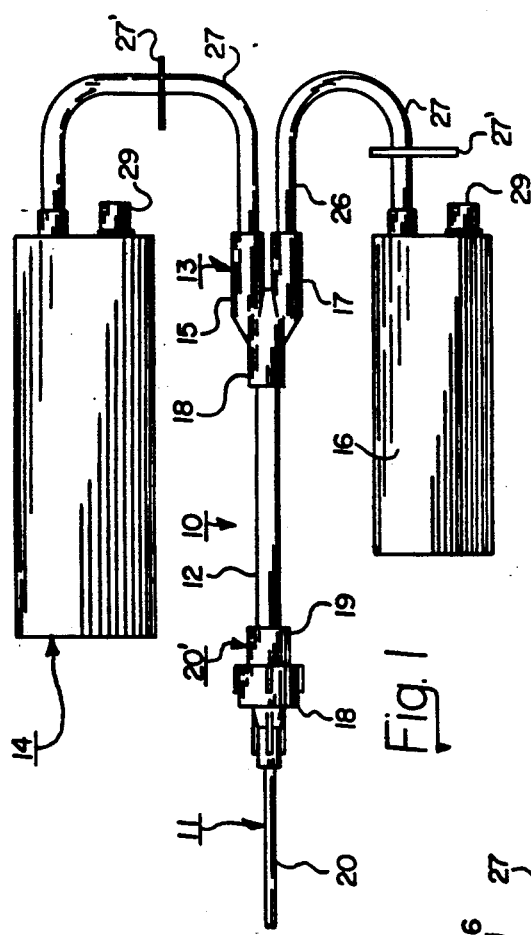

Referring to FIG. 1, the fluid infusion delivery system is constructed in the manner similar to that as described in U.S. Pat. No. 4,867,743. In this respect, the system 10 includes an IV catheter 11 for implantation in a vein of a patient (not shown), a fluid line 12 extending from the catheter 11 and a Y-site connector 13 in the line 12.

The primary pump 14 is connected to the fluid line 12 via one inlet 15 of the connector 13 for continuously delivering a predetermined dose of fluid, i.e. a medicament, into the line 12 under a continuous positive pressure. In addition, a secondary pump 16 is connected to the fluid line 12 via a second inlet 17 of the connector 13 for delivering a second fluid, such as a saline solution, into the line 12 under a pressure sufficient to keep the vein open in the absence of the delivery of medicament from the primary pump 14.

The IV catheter 11 includes a hub 18 having an inlet port 19 at one end and a hollow needle 20 mounted in the hub 18 in communication with the port 19. The needle 20 is sized for entry into a vein as is known. In this respect, the IV catheter 11 may be made of any conventional structure for the purpose of delivering fluid into an accessed vein.

The fluid line 12 extends from the hub 18 and is in communication with the inlet port 19 in order to deliver fluid thereto. In this respect, the fluid line 12 is provided with a luer connection 20' for interconnecting with the hub 18 in known manner.

Figure 2:
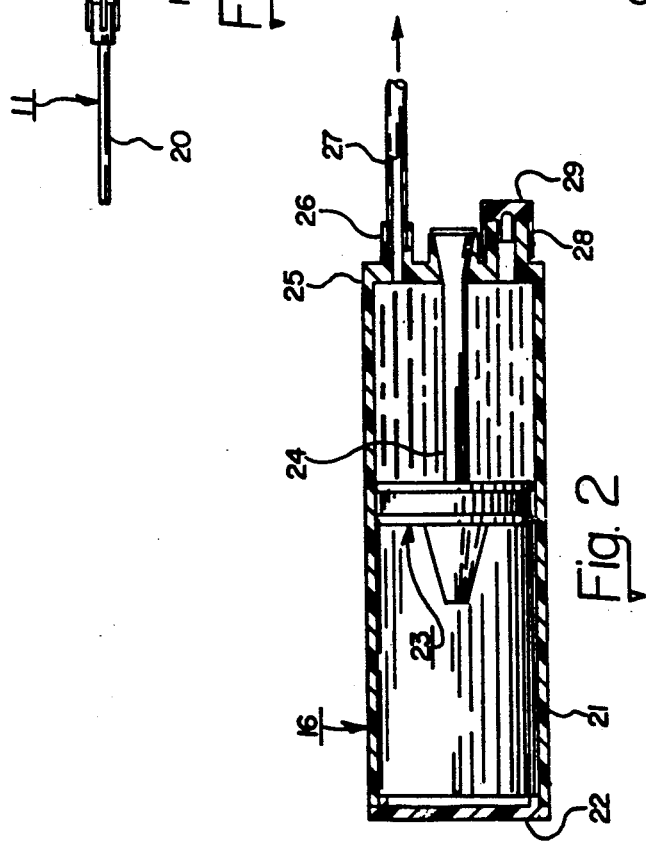
FIG. 2 illustrates a cross-sectional view of a pump for delivering fluid under a continuously applied pressure.

The primary pump 14 and the secondary pump 16 may each be constructed in a similar fashion in order to provide for the delivery of a fluid under a continuous positive pressure. For example, each pump 14, 16 is constructed so as to have mechanical energy storage properties in order to maintain a pressure on the fluid being delivered from the pump. For example, as shown in FIG. 2, the secondary pump 16 may be constructed as described in U.S. Pat. No. 4,867,743 of an open-ended cylinder 21 having a closure cap 22 at one end to close off a chamber, a piston 23 slidably mounted in the cylinder 21 and a stretched elastomeric member 24 (or a spring or the like) to impose a constant pressure on the fluid within the chamber between the piston 23 and the end wall 25 of the cylinder 21. The elastomeric member 24 is secured to and between the piston 22 and the end wall 25 of the cylinder 19. The pump 16 is also constructed with an outlet 26 which receives a delivery line 27 extending to the Y-site connector 13 to expel fluid at a pressure of from 1 to 15 psi as well as an inlet 28 in the end wall 25 for the injection of fluid. A cover 29 is also provided to close the inlet 28.

Referring to FIG. 1, a clip clamp 27' is disposed over each respective line 27 in order to block fluid flow therethrough.

Figure 3:
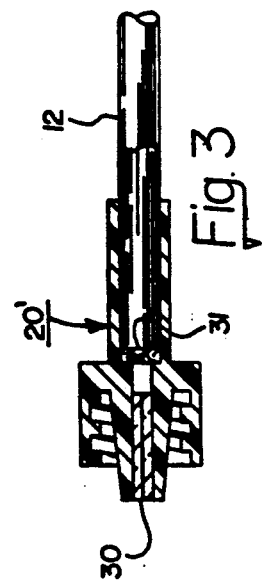
FIG. 3 illustrates a cross sectional view of a restrictor employed at the distal end of a fluid delivery line in accordance with the invention.

Referring to FIG. 3, a restrictor 30 is disposed in the line 12, for example, at the distal end of the line 12 relative to the flow of fluid, i.e. being disposed in the luer connection 20. This restrictor 30 is sized to produce a continual low flow rate at the outlet of the line 12 at a positive fluid pressure. Also, a filter 31 is disposed upstream of the restrictor 30, for example, as described in U.S. Pat. No. 4,867,743 to prevent plugging.

In order to infuse fluid into a vein, the needle 20 of an IV catheter 11 is initially placed in the vein at some point in time. Thereafter, the luer 20' of the fluid delivery line 12 is attached to the hub 18 of the catheter 11 and fluid is passed into the line 12 under a positive pressure by the primary pump 14 with the restrictor 30 maintaining a flow rate of for example from 0.1 to 5 millimeters per hour in order to maintain a positive pressure at the vein. The primary pump 14 delivers fluid at rates up to 100 milliliters per hour and sometimes higher. The flow rate of the secondary pump 16 is low since the function of this secondary pump 16 is to only keep the catheter patent. In this regard, a continuous positive pressure at the catheter exit has been found to retain catheter patency. As a practical matter, this positive pressure is maintained by a continuous flow of fluid from the catheter A flow of 0.1 to 5 millileters per hour can be controlled to retain catheter patency.

As the primary pump 14 is emptied, the pressure generated by the primary pump 14 decreases to a level below the pressure generated by the secondary pump 16. At this time, the dose of medicament has been substantially expelled into the patient. Also, at this time, the secondary pump 16 begins to deliver saline solution through the Y-site connector 14 into the infusion line 12 and thus into the catheter 11 and the vein of the patient. The amount of pressure is sufficient so as to keep the vein open.

The amount of saline solution in the secondary pump 16 and the pressure generated by the secondary pump 16 should be sufficient to permit a patient to have sufficient time to refill the primary pump of medicament or to replace the primary pump 14 with a fresh primary pump filled with medicament.

Referring to FIG. 4, wherein like reference characters indicate like parts as above, the primary pump 14 may be connected in parallel with the secondary pump 16 at a point upstream of the Y-site connector 13. As indicated, a hub, or the like, 32 may have two inlets 33, 34 connected to respective lines 35, 36 from the pumps 14, 16 with a common outlet to a line 37 extending to one inlet port of the connector 13. The second inlet of the connector 13 may be provided with a cover 38 so as to permit the injection of other medicaments or fluids into the infusion line 12.

Referring to FIG. 5, wherein like reference characters indicate like parts as above, the two pumps 14, 16 may be connected to a common hub 39 which has a common outlet 40 to the infusion line 12 leading to the catheter 11. As indicated, this hub 39 has one inlet 41 in communication with the primary pump 14 to receive fluid therefrom and a second inlet 42 in communication with the secondary pump 16 to receive fluid therefrom. As indicated, the two inlets 41, 42 are separated from each other by a common wall. In addition, a restrictor 43 is disposed in the outlet of the hub 39 in order to restrict the flow of fluid therefrom. The restrictor 43 may be constructed as described above with respect to the embodiment of FIG. 3. A filter 44 is also disposed upstream of the restrictor 43 for filtering the flow of fluid therethrough.

Alternatively, as illustrated in FIG. 6, wherein like reference characters indicate like parts as above, a restrictor 45 and a filter 46 may be disposed in each inlet of the hub 34 to cooperate with the flow from the respective pump (not shown).

The two pumps may be constructed to generate pressures relative to each other so that the secondary pump comes into operation after the primary pump has been emptied or has become substantially emptied. Alternatively, the pumps may be operated concurrently so that saline solutions is delivered concurrently with the medicament into the vein of a patient. In this case, the secondary pump continues to infuse saline solution after the primary pump has completed infusion of a medicament dose. For example, the primary pump delivery pressure may be from five (5) to fifteen (15) psi while the secondary pump delivery pressure may be from 0.25 to five (5) psi or higher if the primary pump operates at higher pressures.

Referring to FIG. 7, wherein like reference characters indicate like parts as above, a dual pump 47 may also be used for the infusion of fluids into a fluid line 12 extending to a hub 18 for a catheter or the like. As indicated, the dual pump 47 has a common housing 48 for a primary pump 49 and a secondary pump 50 disposed coaxially within the housing 48. In this respect, the housing 48 includes a pair of end walls 51, 52 and an intermediate third wall 53.

The primary pump 49 includes a piston 54 which is slidably mounted in the housing 48 in spaced relation to the intermediate wall 53 in order to define a drug-receiving reservoir or the like therebetween. In addition, the pump 49 has a compressed spring 55 abutting the piston 54 and the rear end wall 51 of the housing 48. A means is also provided for selectively holding the spring 55 in a compressed state, as viewed, and releasing the spring 55 from the compressed state in order to bias the piston 54 towards the intermediate wall 53 to impose a pressure on a drug in the reservoir therebetween. As illustrated, this means includes a piston rod 56 which is secured to the piston 54 and extends through an elongated opening 57 in the end wall 51 and a cross-piece 58 secured on the end of the rod 56. This cross-piece 58 is sized to abut against the end wall 51 to maintain the spring 55 in a compressed state, as viewed, while being sized to pass through the opening 57 upon rotation of the cross piece 58, for example over an arc of 90° from the position shown. Upon passage of the cross-piece 58 through the opening 57, the spring 55 is released so as to bias the piston 54 towards the intermediate wall 53.

A tube 59 is also disposed within the housing 48 to communicate via an opening 60 in the intermediate wall 53 with the drug receiving reservoir and to communicate with the fluid line 12 in order to conduct a drug therethrough under the pressure generated by the spring 55. As indicated, the line 59 passes into an outlet port in the form of a passageway 61 integrally formed on the end wall 52 of the housing 48 with the fluid line 12 suitably secured to communicate with the passageway 61.

The secondary pump 50 includes an annular piston 62 which is slidably mounted in the housing 48 as well as being slidably mounted on the tube 59 in spaced relation to the front wall 52 in order to define a saline solution receiving reservoir therebetween. In addition, a second spring 63 is provided between the annular piston 62 and the intermediate wall 53 to bias the annular piston 62 towards the front wall 52 in order to pressurize any saline solution within the chamber. In addition, a one-way valve 64 is provided in the front wall 52 between the saline solution reservoir and the fluid line 12 in order to conduct the saline solution therethrough.

The front wall 52 of the housing 48 is also provided with an inlet 65 which communicates with the saline solution reservoir in order to permit delivery of a saline solution into the reservoir under pressure. A cap 66 serves to cover the inlet 65 in sealed relation against the pressure of the saline solution within the reservoir.

The housing end wall 52 also has a second inlet 67 which communicates with the tube 59 in order to permit the filling of a drug into the drug receiving reservoir. This inlet 67 is also covered by a cap 68 in sealed relation against the pressure of any drug in the tube 59.

A suitable clip clamp (not shown) may also be provided on the line 12 in order to block any flow from the pump 47 via the one way valve 64.

The pump 47 can be filled with a drug and saline solution or other suitable fluid media at a remote location from the point of use. The pump can then be transported and/or stored for a period of time. When the pump is to be used, the hub 18 is secured to a catheter implanted in a patient and the clamp (not shown) released so as to permit drug to be dispensed through the line 12 into the catheter (not shown). Next, the cross piece 58 secured to the piston 54 is released so that the piston 54 is driven by the spring 55 to infuse the drug, in the reservoir through the tube 59, outlet port 61 and delivery line 12 to the catheter (not shown). As the piston 54 approaches the intermediate wall 53 the piston 54 will seat in sealing engagement against the opening 60 in the wall 53, so that no further drug can be dispensed. At this time, the pressure in the tube 59 and the outlet one way valve 64 decreases to an extent less than the pressure on the saline solution imposed by the second piston 62. This piston 62 then infuses the saline solution through the valve 64 into the delivery line 12 for infusion into the patient.

Referring to FIG. 8, the dual pump 69 may be constructed with a common housing 70 having a primary pump 71 formed by a bladder 72 which communicates at one end with an outlet port 73 in the housing 70 and a secondary pump 74 formed by a second bladder 75 which is disposed coaxially with the first bladder 72 and communicates via a port 76 which extends through a rear wall 77 of the housing 70 so that the bladder 75 can be filled with a saline solution or other suitable media. In addition, a one-way valve 78 is disposed coaxially of and between the two bladders 72, 75 within a port 79 which extends into the first bladder 72.

As above, an inlet 80 is provided into the first bladder 72 so as to permit delivery of a fluid drug under a pressure sufficient to cause inflation of the bladder 72. A sealing cap 81 is also provided on the inlet 80 to close off the inlet 80 after the bladder 72 has been filled with a drug.

In a similar fashion, after filling of a saline solution under pressure into the second bladder 75, the port 76 can be closed by suitable cap 82 to maintain the saline solution under pressure within the bladder 75.

In use, the pressure exerted by the distended bladder 72 causes the drug to pass through the outlet 73 into the line 12 for delivery to a patient. As the bladder 72 collapses, the differential pressure across the valve 78 increases in the direction of the first bladder 72 so that as the bladder 72 nears emptying, the valve 78 opens to permit the saline solution from the second bladder 75 to flow into the first bladder 72 and, thence, into the line 12 for delivery to the patient.

The invention thus provides a relatively simple system of delivering medicaments to a vein using a disposable ambulatory infusion pump while having "keep vein open" capability upon completion of the delivery of the medicament.

Further, the invention provides an infusion delivery system which prevents backflow into the line and, in particular, diffusion of blood back into the catheter implanted in a vein of a patient. The system thus allows a patient to be ambulatory while the patient's vein remains readily available for medication injection without having to resort to the SASH procedure.

What is claimed is:

1. A fluid infusion delivery system comprising
   an IV catheter for placement in a vein;
   a fluid line extending from said catheter for delivery of a fluid thereto;
   a disposable primary pump connected to said fluid line for delivery a predetermined dose of fluid into said line within a predetermined pressure range; and
   a disposable secondary pump connected to said fluid line for delivery a second fluid into said line under a continuous positive pressure less than said pressure range to maintain said catheter patent in the absence of the delivery of fluid from said primary pump.

2. A system as set forth in claim 1 wherein said primary pump has a reservoir containing a medicament and said secondary pump has a reservoir containing a saline solution.

3. A system as set forth in claim 1 which further comprises a hub having a first inlet in communication with said primary pump to receive fluid therefrom, a second inlet in communication with said secondary pump to receive fluid therefrom and an outlet in communication with said line to deliver fluid thereto from said pumps.

4. A system as set forth in claim 3 which further comprises a restrictor in said outlet of said hub for restricting the flow of fluid into said line and a filter between said restrictor and said inlet to filter the fluid delivered from said pumps.

5. A system as set forth in claim 3 which further comprises a first restrictor in said first inlet for restricting the flow of fluid therethrough, a first filter in said first inlet for filtering the flow of fluid therein, a second restrictor in said second inlet for restricting the flow of fluid therethrough, and a second filter in said second inlet for filtering the flow of fluid therein.

6. A system as set forth in claim 3 wherein said hub is a Y-site connector.

7. A system as set forth in claim 1 which further comprises a common housing having said primary pump and said secondary pump disposed therein.

8. A system as set forth in claim 7 wherein said pumps are coaxially disposed in said housing.

9. A system as set forth in claim 7 wherein said primary pump includes a wall in said housing, a piston slidably mounted in said housing in spaced relation to said wall to define a drug-receiving reservoir therebetween, a compressed said spring in a compressed state and releasing said spring from said compressed state to bias said piston towards said wall to impose a pressure on a drug in said reservoir.

10. A system as set forth in claim 9 wherein said primary pump further comprises a tube communicating with and extending between said reservoir and said fluid line to conduct a drug therethrough.

11. A system pump as set forth in claim 10 wherein said secondary pump includes an annular piston slidably mounted in said housing and on said tube in spaced relation to an end wall of said housing to define a saline solution receiving reservoir therebetween, a second spring between said annular piston and said common wall to bias said annular piston towards said end wall, and a one-way valve between said saline-solution reservoir and said fluid line to conduct saline solution therethrough.

12. A system pump as set forth in claim 7 wherein said primary pump includes a first bladder defining a drug-receiving reservoir in communication with said fluid line, said secondary pump includes a second bladder defining a saline-receiving reservoir in communication with said first bladder, and a one-way valve between said bladders to control a flow of saline from said second bladder into said first bladder.

13. A fluid infusion delivery system comprising
an IV catheter for placement in a vein;
a fluid line extending from said catheter for delivery of a fluid thereto;
a primary pump connected to said fluid line for delivering a predetermined dose of medicament into said line; and
a secondary pump connected to said line for delivering a saline solution into said line under a continuous positive pressure sufficient to keep the vein open after delivery of said medicament dose.

14. A system as set forth in claim 13 which further comprises a hub having a first inlet in communication with said primary pump to receive fluid therefrom, a second inlet in communication with said secondary pump to receive fluid therefrom and an outlet in communication with said line to deliver fluid thereto from said pumps.

15. A dual pump for fluid infusion comprising
a housing having a pair of end walls, a third wall intermediate said end walls and an outlet port in one of said end walls;
a first piston slidably mounted in said housing to define a drug-receiving reservoir with said third wall;
a compressed spring between said first piston and the other of said end walls;
means for selectively holding said spring in a compressed state and releasing said spring from said compressed state to bias said first piston towards said wall to impose a pressure on a drug in said reservoir;
a tube in communication with and extending between said reservoir and said outlet port to conduct a drug therethrough under pressure;
an annular piston slidably mounted in said housing and on said tube in spaced relation to said one end wall to define a saline-solution receiving reservoir therebetween;
a second spring to bias said annular piston towards said one end wall to impose a pressure on saline in said saline-solution receiving reservoir; and
a one-way valve between said saline-solution receiving reservoir and said outlet port to conduct saline solution therethrough.

16. A dual pump as set forth in claim 15 wherein said housing includes a first inlet in communication with said tube for filling a drug with said drug-receiving reservoir and a second inlet in communication with said saline-solution receiving reservoir for delivering a saline solution thereto.

17. A dual pump as set forth in claim 15 wherein said third wall has an aperture in coaxial communication with said tube.

18. A dual pump as set forth in claim 15 wherein said second spring is disposed between said third wall and said annular piston.

19. A fluid infusion delivery system comprising
an IV catheter for placement in a vein;
a fluid line extending from said catheter for delivery of a fluid thereto;
a disposable primary pump connected to said fluid line for delivering a predetermined dose of fluid into said line within a predetermined pressure range;
a disposable secondary pump connected to said fluid line for delivering a second fluid into said line under a continuous positive pressure less than said predetermined pressure range to maintain said catheter patent in the absence of the delivery of fluid from said primary pump; and
a one-way valve between said secondary pump and said fluid line to prevent a flow of fluid from said primary pump into said secondary pump.

20. A system as set forth in claim 1 wherein said primary pump has a reservoir containing a medicament and said secondary pump has a reservoir containing a saline solution.

* * * * *

UNITED STATES PATENT AND TRADEMARK OFFICE
CERTIFICATE OF CORRECTION

PATENT NO. : 5,188,603
DATED : February 23, 1993
INVENTOR(S) : Vincent L. Vaillancourt It is certified that error appears in the above-identified patent and that said Letters Patent is hereby corrected as shown below:

Column 10, line 43, change "claim 1" to -claim 19-

Signed and Sealed this

Fourth Day of January, 1994

Attest:

*Attesting Officer*

BRUCE LEHMAN

*Commissioner of Patents and Trademarks*